(12) United States Patent  (10) Patent No.: US 8,701,212 B2
Daniels et al.  (45) Date of Patent: Apr. 22, 2014

(54) ELONGATED GUIDE, AND VISOR REMOVABLY MOUNTABLE THERETO

(71) Applicant: 3M Innovative Properties Company, St. Paul, MN (US)

(72) Inventors: Björn Daniels, Vikarbyn (SE); Niklas Lilenthal, Djura (SE); Marcus T. R. Wiederkehr, Leksand (SE); Jonas N. A. Frejd, St. Skedvi (SE); Mats U. Sernfält, Leksand (SE); Oskar E. Juhlin, Gustavsberg (SE); Arne O. Linderstrand, Leksand (SE); Stefan G. Strandberg, Stockholm (SE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/627,571

(22) Filed: Sep. 26, 2012

(65) Prior Publication Data

US 2014/0082810 A1  Mar. 27, 2014

(51) Int. Cl.
*A42B 3/22* (2006.01)

(52) U.S. Cl.
USPC .................................................. 2/8.2

(58) Field of Classification Search
USPC ......... 2/8.2, 5, 6.1, 9, 10, 410, 422, 423, 424, 2/425, 6.3, 6.4, 6.5, 909
See application file for complete search history.

(56) References Cited

U.S. PATENT DOCUMENTS

| | | | |
|---|---|---|---|
| D168,057 S | 10/1952 | Margwarth | |
| 2,798,221 A | 7/1957 | Bailey | |
| 3,237,202 A | 3/1966 | Aileo | |
| 3,315,272 A | 4/1967 | Olt | |
| 3,400,407 A | 9/1968 | Aileo | |
| 3,601,813 A | 8/1971 | Aileo | |
| 3,748,657 A * | 7/1973 | Aileo | 2/6.4 |
| 3,864,756 A * | 2/1975 | Desimone | 2/423 |
| 4,028,739 A * | 6/1977 | Bell et al. | 2/6.3 |
| 4,280,491 A | 7/1981 | Berg | |
| 4,432,100 A * | 2/1984 | Bates | 2/424 |
| 4,434,514 A | 3/1984 | Sundahl | |
| 4,922,550 A * | 5/1990 | Verona et al. | 2/6.2 |
| 5,604,930 A | 2/1997 | Petit | |
| 7,093,302 B1 | 8/2006 | Burns | |
| 7,219,370 B1 | 5/2007 | Teetzel | |
| 7,546,645 B2 | 6/2009 | Goodhand | |
| 2004/0143888 A1 | 7/2004 | Bataille | |
| 2007/0245467 A1 | 10/2007 | Lilenthal | |
| 2012/0084904 A1 | 4/2012 | Paulson | |

FOREIGN PATENT DOCUMENTS

| | | |
|---|---|---|
| CA | 2570095 | 6/2008 |
| DE | 1735005 C | 6/1972 |
| DE | 102007053190 | 5/2009 |
| EP | 2 271 407 | 1/2011 |
| FR | 2532528 | 3/1984 |
| IL | 115326 | 6/1998 |
| WO | 2009-123809 | 10/2009 |
| WO | WO 2009/148335 | 12/2009 |
| WO | WO 2012/007476 | 1/2012 |
| WO | 2012-047936 | 4/2012 |

OTHER PUBLICATIONS

International Search Report, PCT/US2013/059211, mailed Dec. 11, 2013, 3 pages.

* cited by examiner

*Primary Examiner* — Tejash Patel
(74) *Attorney, Agent, or Firm* — Kenneth B. Wood (57) ABSTRACT

An elongated guide that is removably attachable to a hardhat and a visor that is removably mountable to the elongated guide.

25 Claims, 7 Drawing Sheets

ELONGATED GUIDE, AND VISOR REMOVABLY MOUNTABLE THERETO

BACKGROUND

Hardhats for head protection, and visors for eye protection, have found wide use in applications such as industrial production, building construction, and the like.

SUMMARY

In broad summary, herein is disclosed an elongated guide that is removably attachable to a hardhat and a visor that is removably mountable to the elongated guide. These and other aspects of the invention will be apparent from the detailed description below. In no event, however, should the above summary be construed to limit the claimable subject matter, whether such subject matter is presented in claims in the application as initially filed or in claims that are amended or otherwise presented in prosecution.

Like reference numbers in the various figures indicate like elements. Some elements may be present in identical or equivalent multiples; in such cases only one or more representative elements may be designated by a reference number but it will be understood that such reference numbers apply to all such identical elements. Unless otherwise indicated, all figures and drawings in this document are not to scale and are chosen for the purpose of illustrating different embodiments of the invention. In particular the dimensions of the various components are depicted in illustrative terms only, and no relationship between the dimensions of the various components should be inferred from the drawings, unless so indicated. Terms such as front, forward, and the like, indicate a direction toward the forehead portion of a hardhat; terms such as rear, rearward, back, and the like, indicate a direction away from the forehead portion and toward the occipital portion of a hardhat. As used herein as a modifier to a property or attribute, the term generally, unless otherwise specifically defined, means that the property or attribute would be readily recognizable by a person of ordinary skill but without requiring absolute precision or a perfect match (e.g., within +/−20% for quantifiable properties). The term substantially, unless otherwise specifically defined, means to a high degree of approximation (e.g., within +/−10% for quantifiable properties) but again without requiring absolute precision or a perfect match. Terms such as same, equal, uniform, constant, strictly, and the like, are understood to be within the usual tolerances or measuring error applicable to the particular circumstance rather than requiring absolute precision or a perfect match.

DETAILED DESCRIPTION

Figure 1:
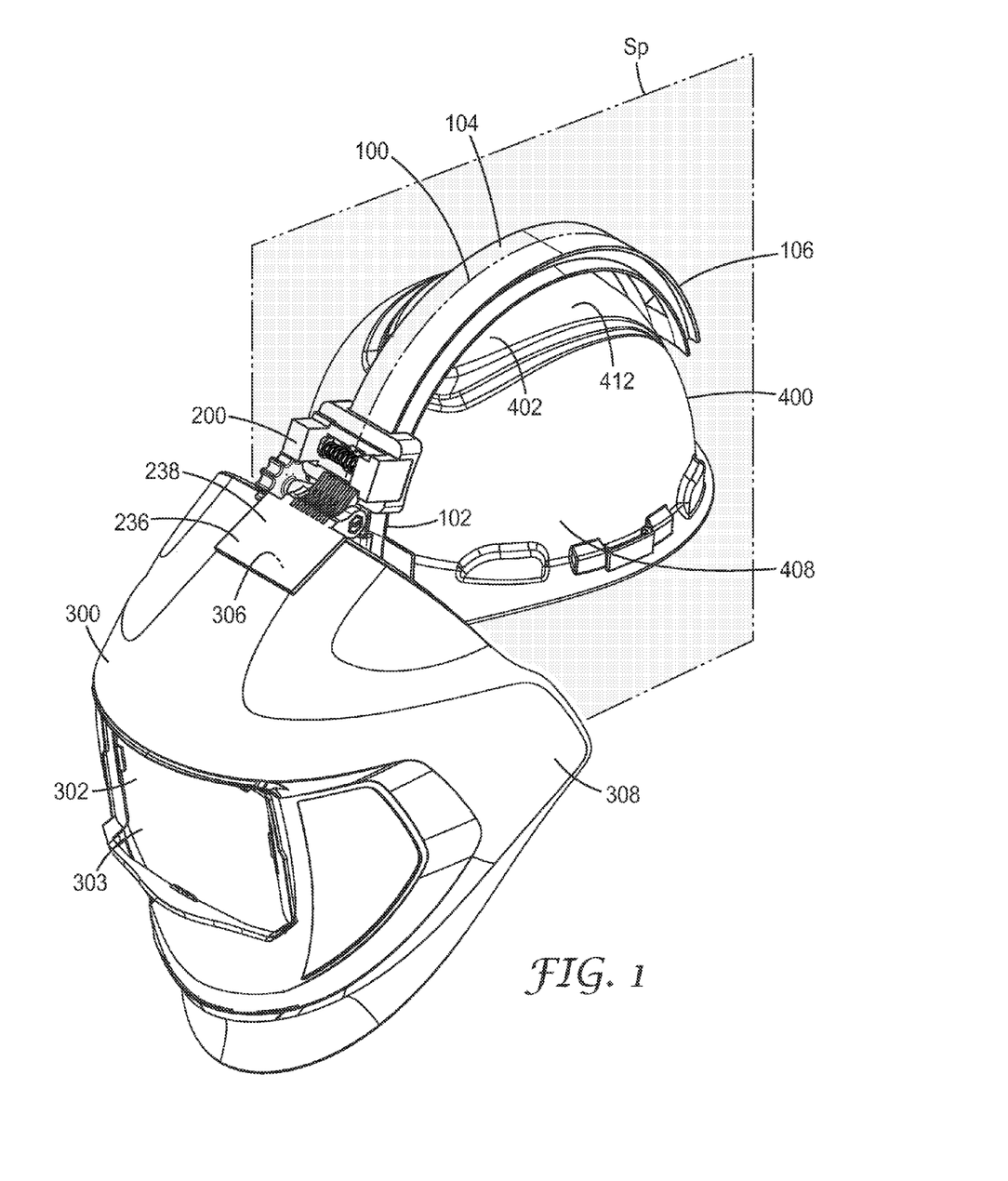
FIG. 1 is a front-side perspective view of an exemplary elongated guide that is removably attached to an exemplary hardhat and that slidably supports an exemplary visor, with the visor shown in a first, shielding position.
Figure 2:
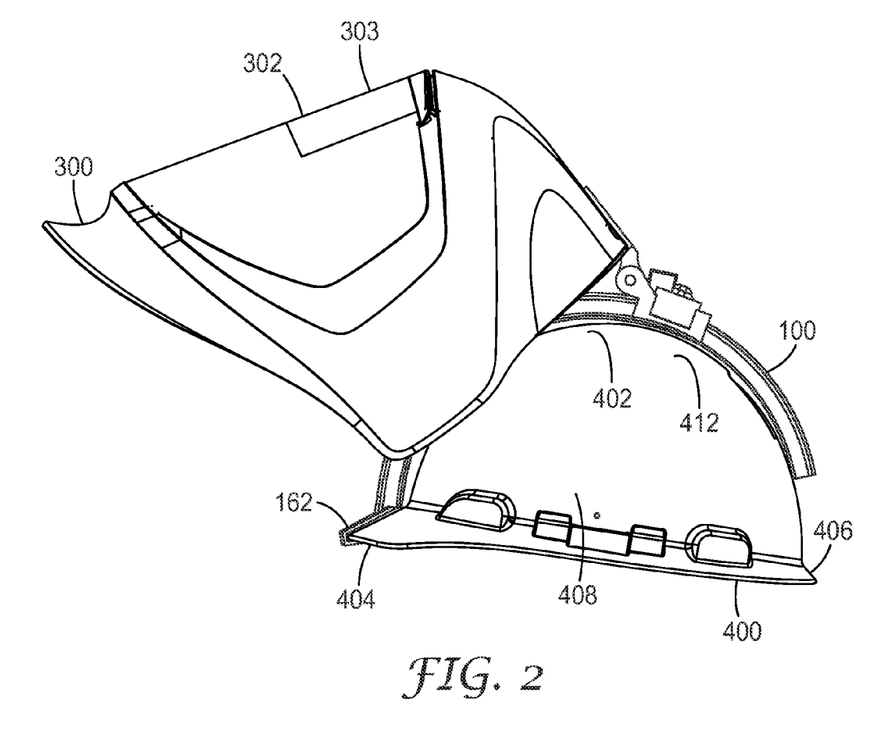
FIG. 2 is a side view of the assembly of FIG. 1, with the visor in a second, retracted position.

Shown in FIG. 1 in front-side perspective view is an exemplary elongated guide 100 that slidably supports an exemplary visor 300. Elongated guide 100 is removably attachable to hardhat 400, and, in some embodiments, can be supplied already attached to a hardhat 400 (e.g., as shown in FIG. 1). In other embodiments, elongated guide 100 can be supplied separately and can be attached to hardhat 400 e.g. by a user of hardhat 400. Visor 300 is removably mountable to elongated guide 100 so as to be slidably supported thereby, so that visor 300 can be slidably moved generally forward and rearward along the long axis of elongated guide 100, from at least a first, shielding position (in which the visor shields the eyes of a user of hardhat 400) as shown in FIG. 1, to a second, refracted (non-eye-shielding) position as shown in FIG. 2.

The term "hardhat" is used broadly herein to denote any head-protection apparatus comprising a hard shell that can protect at least an upper portion of a user's head from impact forces (e.g., from falling objects, collisions with hard surfaces and so on). As such, a hardhat may be any of the well-known head-protective hardhats that are commonly used in industrial and construction environments. However, the term hardhat also encompasses bump caps for general use, athletic helmets, military helmets, firefighter's helmets, and so on. In some specific embodiments, a hardhat may meet the standards outlined in ANSI/ISEA Z89.1 as specified in 2009; and, in various embodiments, a hardhat may be classified as a Type I hardhat or a Type II hardhat under these standards. In various embodiments, a hardhat may comprise a front brim (i.e., a flange, which may serve e.g. as an eyeshade) 404, a rear rim 406, a crown area 402, a temple/ear area 408, and a radially outward-facing surface 412, as variously seen in FIGS. 1 and 2. Although not shown in these Figures, in some embodiments (e.g., when the hardhat is in the form of a firefighter's helmet) the hardhat may comprise a rear brim (either in addition to, or instead of, a front brim). A hardhat may comprise a harness (including e.g. a headband) for adjustably fitting the hardhat to a user's head (with e.g. a space provided between the harness and the hard shell of the hardhat); one or more cushions or padding, a chinstrap, or some combination of any or all of these features. The hard shell of a hardhat may be made of any suitable (e.g., impact resistant) material that can be formed into the desired shape; e.g. a thermoplastic molding material, a thermoset material, or the like. Such materials may be optionally reinforced with mineral fillers, glass fibers, carbon fibers, and so on, as desired to enhance their physical properties.

The term "visor" is used broadly herein to denote any eye-protection apparatus that comprises a window portion that, when the visor is in a first, eye-shielding position (e.g., as shown in FIG. 1), allows at least some electromagnetic radiation (e.g., visible light) to pass therethrough so as to reach the user's eyes. This may be provided, for example, by including window portion 302 with a light transmissive pane 303 as shown in FIG. 1.

In some embodiments, light transmissive pane 303 of window 302 may be configured to block high intensity light. In this context, "light" means electromagnetic radiation of a wavelength that might be capable of damaging the eyes of a user, or of causing perceived discomfort to the user. Such light includes at least visible light, and may also include infrared and/or ultraviolet radiation, whether or not such radiation is perceptible to the user. In this context, "high intensity" light means light that is present at an intensity (e.g. such as that emitted by a device such as an arc welder) such that it might be capable of damaging the eyes of a user, or of causing perceived discomfort to the user. The light-blocking properties of pane 303 may be characterized e.g. by a Shade Number as is commonly known in the art. Thus, in various embodiments pane 303 may exhibit a Shade Number of at least about 4, 6, 8, 10, or 12 (or, of any suitable value). In some embodiments, pane 303 may comprise an adjustable lens, an auto-darkening filter, or the like (e.g., so that the Shade Number may be varied). A visor with this type of pane might find use e.g. in industrial operations, for example welding (e.g. arc welding, torch welding, acetylene welding), cutting (e.g. laser cutting, acetylene cutting), brazing, soldering and the like.

In general, however, visor 300 can be any suitable visor as desired for any eye-protection function, whether such a function serves to protect the user's eyes from electromagnetic radiation (as discussed above), from solid matter (e.g., from particulate debris or the like), or from liquid matter (e.g., from splashing liquids and the like). For example, visor 300 may be a so-called grinding visor, in which the pane of the visor might not necessarily provide any particular protection from electromagnetic radiation (e.g., it might serve primarily to protect the users eyes from flying debris), or it may be any kind of general-purpose eye-protection and/or face-protection visor. Such a visor and a pane thereof may each be made of any suitable material, as chosen e.g. from thermoplastic molding materials with suitable physical properties (and optical properties, in the case of a pane). For example, a pane could be made of glass, transparent plastic, metal mesh (e.g., steel mesh), and so on.

As mentioned above, elongated guide 100 is removably attachable to hardhat 400, and can be supplied already attached to hardhat 400 (e.g., as shown in FIG. 1); or, can be supplied separately and can then be removably attached to hardhat 400 by a user of hardhat 400. Elongated guide 100 may comprise e.g. an elongated main body made of any suitable material (e.g. metal, thermoplastic molding material, etc.), as well as any number of ancillary components (e.g., straps, clips, latches, etc.) as desired for various purposes. Elongated guide 100 is configured so that visor 300 is removably mountable thereto, and is further configured so that when visor 300 is removably mounted thereto, elongated guide 100 slidably supports visor 300 so that visor 300 can be moved generally along the long axis of elongated guide 100 at least between the first and second (shielding and retracted) positions described above and shown in exemplary manner in FIGS. 1 and 2.

Elongated guide 100 is configured so that when it is attached to hardhat 400, the long axis of elongated guide 100 is at least generally coincident with the sagittal plane of hardhat 400 (the sagittal plane being the imaginary plane that passes vertically through the head of a user (wearer) of the hardhat and that divides the head and hardhat into generally equal and symmetrical right and left portions, which sagittal plane is identified as $S_p$ in FIG. 1). By at least generally coincident is meant that the long axis of the elongated guide is oriented at an angle of within plus or minus about 25 degrees of the sagittal plane. In some embodiments the long axis of the elongated guide may be oriented within plus or minus about 10 degrees of the sagittal plane; in further embodiments, it may be oriented with plus or minus about 2 degrees of the sagittal plane, e.g. as shown in FIG. 1. By at least generally coincident is also meant that the long axis of the elongated guide is located at distance of no greater than about 4 cm to either lateral side of the sagittal plane of the hard hat, at all points along the elongated length of the guide. In further embodiments, the long axis of the elongated guide may be located at a distance of no greater than about 2 cm, or 1 cm, to either lateral side of the sagittal plane of the hardhat. In particular embodiments, the long axis of the elongated guide is aligned with (e.g., overlaps) the sagittal plane of the hardhat. In specific embodiments, the lateral center of the elongated guide may be substantially, or strictly, aligned with the sagittal plane of the hardhat, at least at some points along the elongated length of the guide. All of these embodiments can be contrasted with, for example, an arrangement in which a guide is offset from the sagittal plane of a hardhat to which it is attached, by a distance of more than 4 cm. In particular, such embodiments can be contrasted with guides that may run from the temple portion of a hardhat, back along the side of the hardhat.

It is noted that elongated guide 100 may often be at least generally linear when viewed from a perspective aligned with the sagittal plane (e.g., when a hardhat and the attached elongated guide are viewed from directly vertically above). However, elongated guide 100 may often be generally arcuate when viewed from a perspective generally normal to the sagittal plane (e.g., when viewed from the side, as in the view of FIG. 2). It will be appreciated that such an arcuate design of the elongated guide may conveniently allow the elongated guide to at least generally follow the curvature of a hardhat to which the elongated guide is attached. It will thus be understood that the aforementioned long axis of the elongated guide may often be an arcuate long axis. It will also be understood that the curvature of the elongated guide can be chosen as desired, and that the guide does not have to be provided strictly as an arc of a circle nor does it have to exactly match the curvature of a hardhat to which it is attached. For example, in some embodiments an elongated guide may comprise a rear portion that diverges from the radially-outward surface of the hardhat rather than strictly following the curvature of the hardhat. (Thus in general, the curvature of the elongated guide is not required to remain constant along the elongated length of the guide).

Figure 3:
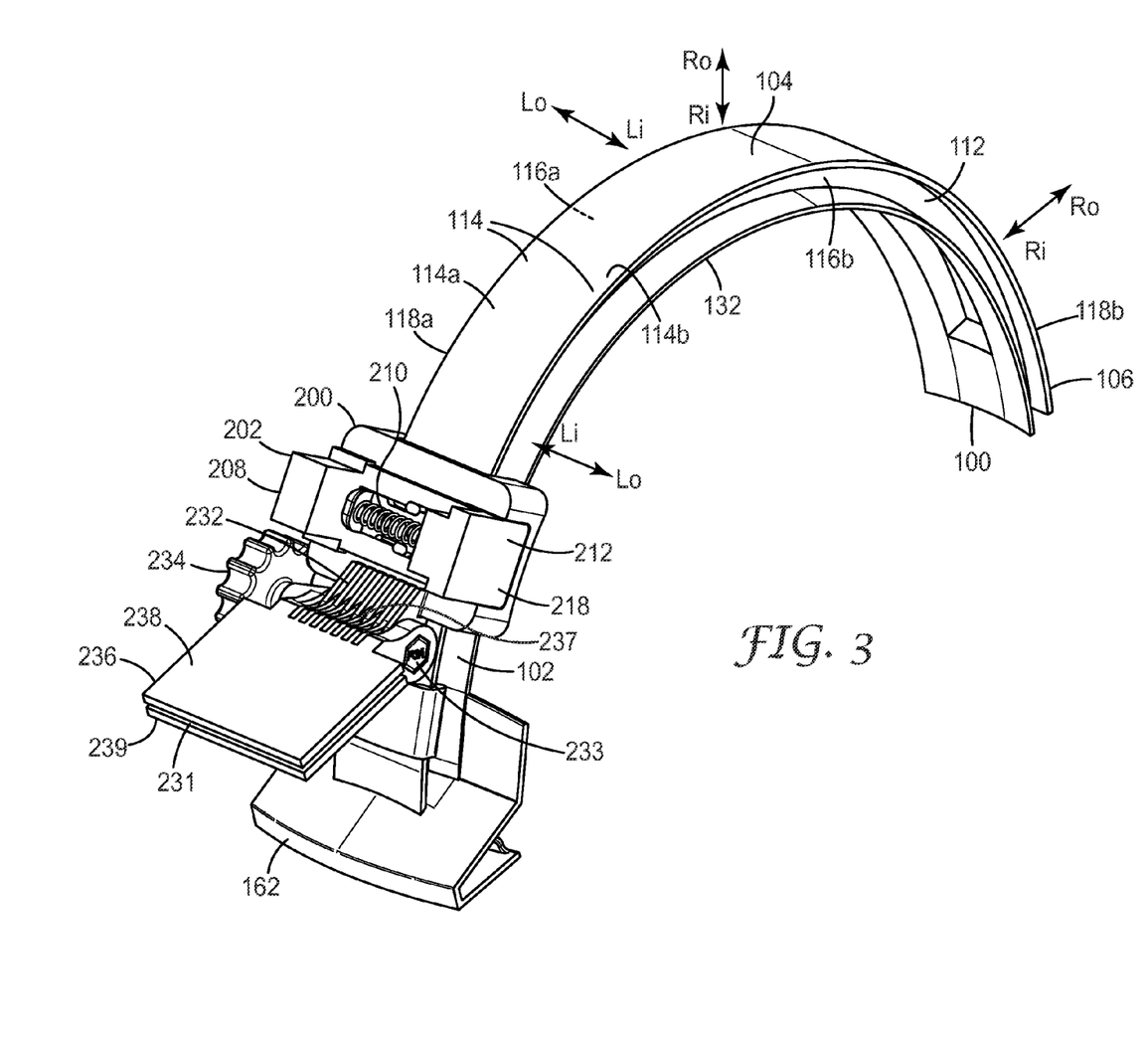
FIG. 3 is a front-side perspective view of an exemplary elongated guide and an exemplary carriage that is removably mounted thereto and slidably supported thereby.
Figure 4:
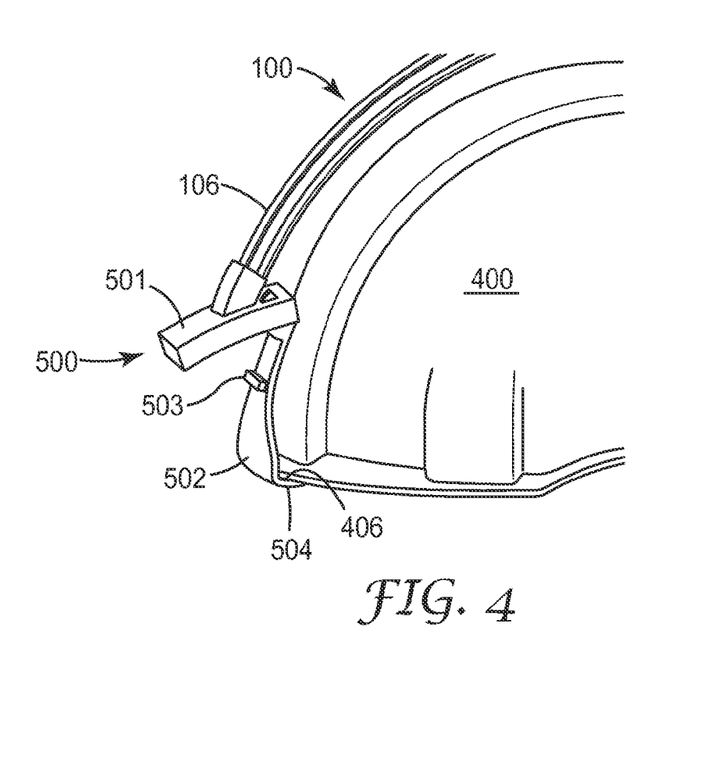
FIG. 4 is a side-rear perspective view of a portion of an exemplary elongated guide and of an exemplary rear attachment mechanism that can be used to attach a rear section of the elongated guide to a hardhat.
Figure 6:
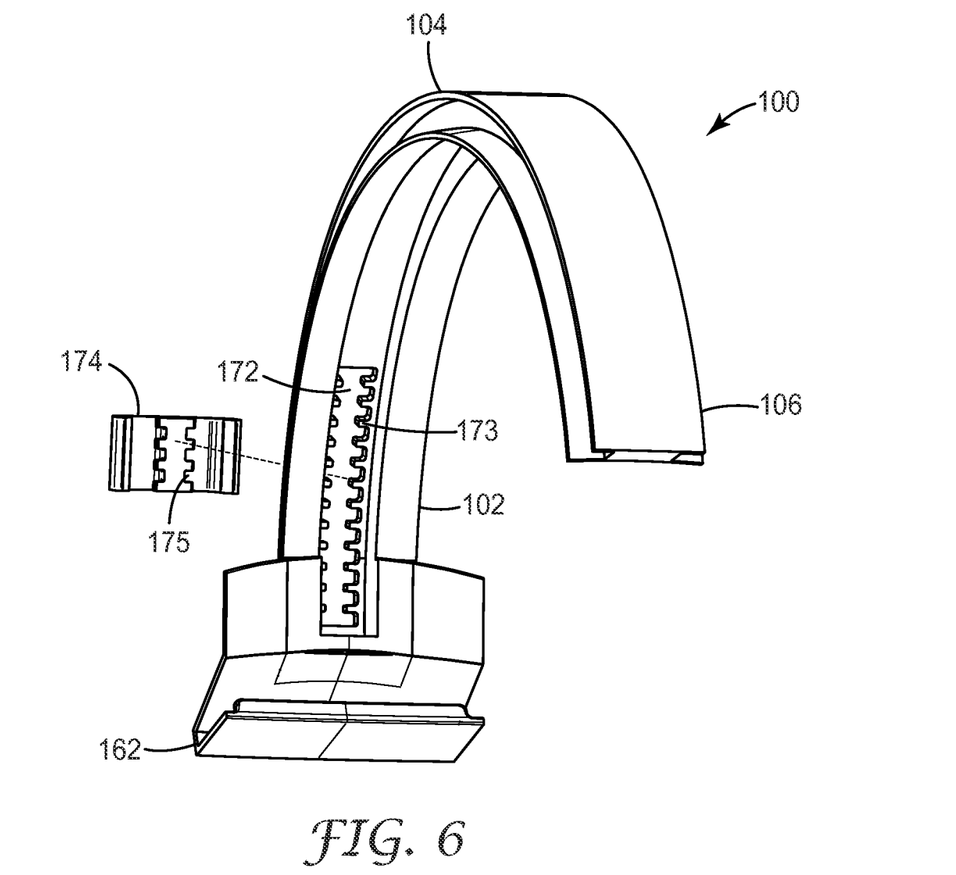
FIG. 6 is a rear perspective partially exploded view of an exemplary elongated guide and a positionable insert that can be used to set an end-stop for a carriage.

The elongated guide may be removably attached to a hardhat in any suitable manner. By removably attachable is meant that the elongated guide can be attached to a hardhat, and removed therefrom, manually (i.e., by hand) by the user, without requiring the use of any special tools (such as e.g. a screwdriver, pliers, wrench, or the like). By this is also meant that neither the elongated guide nor the hardhat is unacceptably damaged or destroyed in the process of removing the elongated guide from the hardhat. It may be convenient to attach the elongated guide to a hardhat by way of a front attachment mechanism, e.g., by way of front attachment bracket 162 as shown in detail in FIGS. 3 and 6, which bracket may be fitted onto a front brim (e.g., bill or eyeshade) 404 of a hardhat 400, as shown e.g. in FIG. 2. It may also be convenient to attach the elongated guide to a hardhat by way of a rear attachment mechanism (no such rear attachment mechanism is shown in FIGS. 1-3, so that other components can be presented more easily). In some embodiments, such a rear attachment mechanism may be an adjustable mechanism, by which is meant that the mechanism can be adjusted e.g. so that the elongated guide can be attached to hardhats of different sizes, shapes, configurations, etc. An exemplary rear attachment mechanism 500 is shown in FIG. 4, comprising a first portion 501 that is attachable to a rear section 106 of the elongated guide, and a second portion 502 with rear attachment bracket 504 that is attachable to rear rim 406 of the hardhat, with first and second portions 501 and 502 being pivotably connected to each other so that first portion 501 can be rotated toward second portion 502 so as to be secured to portion 502 (e.g., by way of latch 503) so as to tighten the attachment mechanism to secure the elongated guide to the hardhat. It will be appreciated however that the attachment mechanism of FIG. 4 is only a representative example and that any attachment mechanism, e.g. any adjustable mechanism as might rely on one or more adjusting knobs, slidable adjustments (e.g., serrated pull-through members) or the like, may be used. And, of course, in various embodiments a front attachment mechanism might also be adjustable. In some embodiments, such front and rear attachment mechanisms may be the only ones used to attach the elongated guide to the hardhat. In other embodiments, some other attachment mechanism might be used at some other location. For example, a crown portion (e.g., 104) of the elongated guide might be attached to a crown portion (e.g., 402) of the hardhat. In addition, any portion, e.g. a crown portion, of the elongated guide may comprise an adjustment mechanism whereby e.g. the length of the elongated guide can be adjusted so that the guide can be tightly attached to any particular hardhat.

A visor may be removably mounted to the elongated guide in any suitable manner. By removably mounted is meant that the visor is placed into a configuration in which it is slidably supported by the elongated guide so that it can be slidably moved back and forth generally along the long axis of the guide as desired by the user, but is secured to the guide so that it will not become dislodged from the guide unless action to do so is taken by the user (as described in detail later herein).

In some embodiments, the removable mounting of the visor onto the elongated guide, and the slidable supporting of the visor by the elongated guide, may be facilitated by a carriage, as represented by exemplary carriage 200 as shown e.g. in FIG. 3. By carriage is meant an article (e.g., whether made of a single part, or an assembly of parts) that is connectable to a visor and that is engageable to an elongated guide in such manner that the carriage is slidably movable generally along the long axis of the guide but will not become dislodged from the guide unless action to do so is taken by the user. The carriage and parts thereof may be made of any suitable material(s) (e.g. metal, thermoplastic molding material, etc.). If desired, various surfaces (e.g., radially-inward and/or radially-outward surfaces) of the carriage may be curved so as to at least approximately match the curvature of the elongated guide, to enhance the ease of slidably moving the carriage along the guide. In some embodiments, such a carriage is removably engagable to the guide, meaning that it can be engaged to the guide and disengaged therefrom, manually (by hand) by the user, without requiring the use of any special tools. In some embodiments of this type, the carriage may be non-removably connectable to a visor, meaning that the visor is not removable from the visor without unacceptably damaging or destroying the visor and/or the carriage; and/or that the visor may be removable from the carriage only by the use of one or more tools rather than manually (by hand). In other embodiments of this type, the carriage may be removably connectable to a visor, meaning that it can be disconnected therefrom by hand without damaging or destroying the visor or the carriage. In the exemplary illustration shown in FIGS. 1 and 2, carriage 200 is connected to visor 300 by way of the carriage comprising a bracket 236 comprising first and second members 238 and 239 that define slot 231 therebetween (as shown in detail in FIG. 3), which slot may receive a flange 306 of visor 300 thereinto such that flange 306 is pinned between members 238 and 239, which members may be tightened together so as to hold the visor securely to the carriage. Such a connection may be configured so that visor 300 may be released from carriage 200 by hand; or, it may be configured so that the use of a tool such as a screwdriver, wrench, etc. is required. If desired, a bolt (not shown) may pass through aligned openings in the first and second members and the visor flange, so as to enhance a non-removable connecting of the visor to the carriage.

Such a carriage may be configured so that a user can grasp the carriage (and/or the visor connected thereto) with his or her hand(s) and can move the carriage and visor forward and rearward generally along the long axis of the elongated guide, at least between a first, eye-shielding position and a second, refracted position. In some embodiments, this moving may be accomplished with the use of only one hand. The carriage may be designed so that the ease with which the visor can be slidably moved (as governed e.g. by the friction between various components of the carriage and the guide) is in a desired range; for example, so that the visor is not so easy to move that it may undesirably move e.g. in response to a motion of the user's head, but so that the visor can readily be moved by the user by grasping the visor (or the carriage) with one hand and applying force in a forward or rearward direction along the long axis of the elongated guide.

In some embodiments, the visor may be passively held in the first, shielding position (e.g., the weight of the visor may exert a downward force so as to hold the visor in the first position). In other embodiments, the visor may be actively held in the first position (e.g., by means of a latch that is closed to hold the visor in the first position until the latch is opened (released) by the user). Such a latch may be configured so that it must be manually closed by the user in order to hold the visor in the first position; or, it may be configured so that moving the visor into the first position automatically closes the latch. Such an automatically closable latch might be provided e.g. by a biased (e.g., spring-loaded) member of the carriage in combination with a recess provided at a desired location of the elongated guide. Similarly, the visor may be passively or actively held in the second, retracted position of the visor, e.g. by a manually closable latch or by an automatically closable latch.

In some embodiments, a carriage may be configured to allow the carriage (and a visor connected thereto) to be engaged to the elongated guide manually (by hand) by the user. In further embodiments this may be accomplished by the use of only a single hand. In specific embodiments, the elongated guide and the carriage may be configured so that the carriage is engageable with the elongated guide by moving the carriage generally radially inward toward the elongated guide from a position radially outward of the elongated guide. As referred to here and elsewhere herein (and as seen most clearly with reference to FIG. 3); by radially inward is meant a direction that progresses generally toward the concave side of the guide (e.g., toward a hardhat to which the guide is attached). By radially outward is meant a direction that progresses generally away from the concave side of the guide (e.g., away from a hardhat to which the guide is attached). Exemplary radially inward-outward directions $R_i$ and $R_o$ are shown in FIG. 3.

Figure 7:
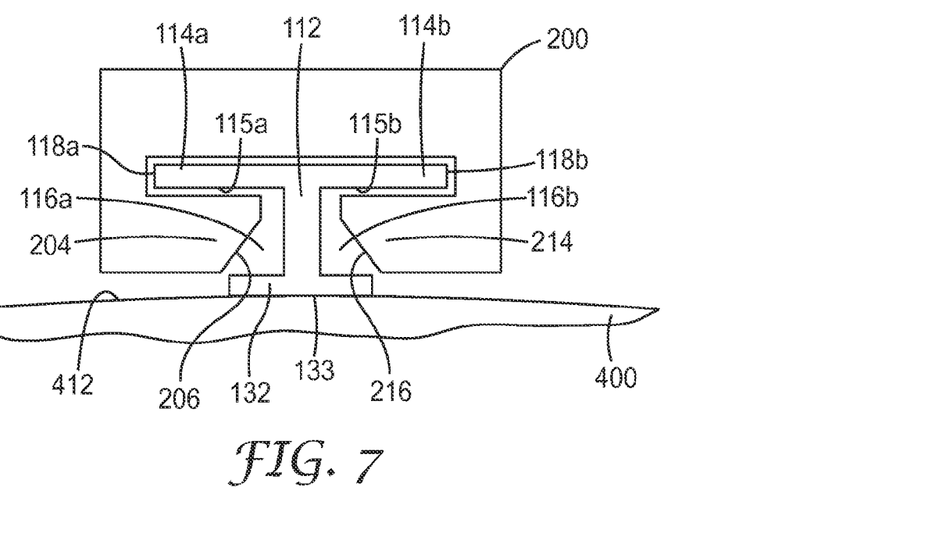
FIG. 7 is a representation in generic cross-sectional view, of an exemplary elongated guide and an exemplary carriage slidably supported thereby.

Any suitable design of the elongated guide and of the carriage can be used to achieve the result that a carriage can be engaged with the elongated guide by being moved generally radially inward theretoward. One design which may be useful for such purposes is the exemplary carriage 200 shown in FIG. 3 and in further detail in FIG. 5 (a more generic representation of this general type of carriage is shown in FIG. 7). Such a carriage may be conveniently used with an elongated guide of the general type shown in FIG. 3, in which the elongate guide is provided in the form of an elongated rail comprising a main rib 112 with a long axis that defines the long axis of the elongated guide and with the elongated rib further comprising a radially outward, laterally-flared flange 114. Here and elsewhere herein, the term laterally denotes a direction generally normal to the sagittal plane with which the elongated guide is at least generally coincident; laterally inward means toward the sagittal plane, and laterally outward means away from the sagittal plane (exemplary laterally inward and outward directions $L_i$ and $L_o$ are shown in FIG. 3). The radially-outward, laterally-flared flange 114 of the elongated rail at least partially defines (e.g., by way of first and second flange portions 114a and 114b) first and second elongated channels 116a and 116b. Such elongated channels may conveniently be laterally-outwardly open (as shown in exemplary manner in FIG. 3); a radially-outward limit of such a channel may be defined at least in part e.g. by a flange portion (e.g., 114a), and a laterally-inward limit of such a channel may be defined at least in part e.g. by main rib 112. In some embodiments a radially-inward limit of such an elongated channel may be defined at least in part by a second, radially-inward flange 132 (such a flange may enhance the stability, stiffness, and/or strength, etc., of the elongated guide, and may give the elongated guide a generally I-beam shaped cross-sectional appearance, as shown in FIG. 3). Or, in other embodiments, such a second, radially-inward flange may be very small or nonexistent, in which case the elongate rail may comprise a generally T-shaped cross-sectional appearance (as shown in the generic representation of FIG. 7), and in which case the radially-inward limit of an elongated channel may be defined at least in part by a radially-outward surface 412 of the hardhat to which the guide is attached. It will be noted that the various flanges, ribs, etc. as shown in FIG. 3 are depicted as generally continuous. However, such flanges, ribs and the like do not necessarily have to be continuous, as long as any discontinuities, interruptions etc. do not unacceptably impact the co-functioning of the carriage and elongated slide as described herein. In additional, the flanges, ribs, etc., can have any desired cross-sectional shape (i.e., they are not limited to the generally rectangular cross-sectional shapes depicted in FIGS. 3 and 7).

With features of the exemplary elongated guide of FIG. 3 having been described, the configuring of a carriage to allow the engaging of the carriage to such an elongated guide by moving the carriage radially-inward toward the guide can now be discussed. One way of achieving such an arrangement is by a carriage of the type shown in exemplary manner in FIG. 5. (A more generic representation of this approach is shown in cross-sectional view in FIG. 7.) In embodiments of this type, a carriage 200 may comprise first and second laterally-inwardly-facing, oppositely-facing fins 204 and 214, that are configured so that when the fins are in a first, engaged position at least portions of the fins respectively extend sufficiently laterally inwards into the first and second elongated channels 116a and 116b to maintain the carriage in an engaged condition with the elongated guide. That is, the interference of the flange portions 114a and 114b with fins 204 and 214 prevents the carriage from being dislodged from the elongated guide.

Figure 5:
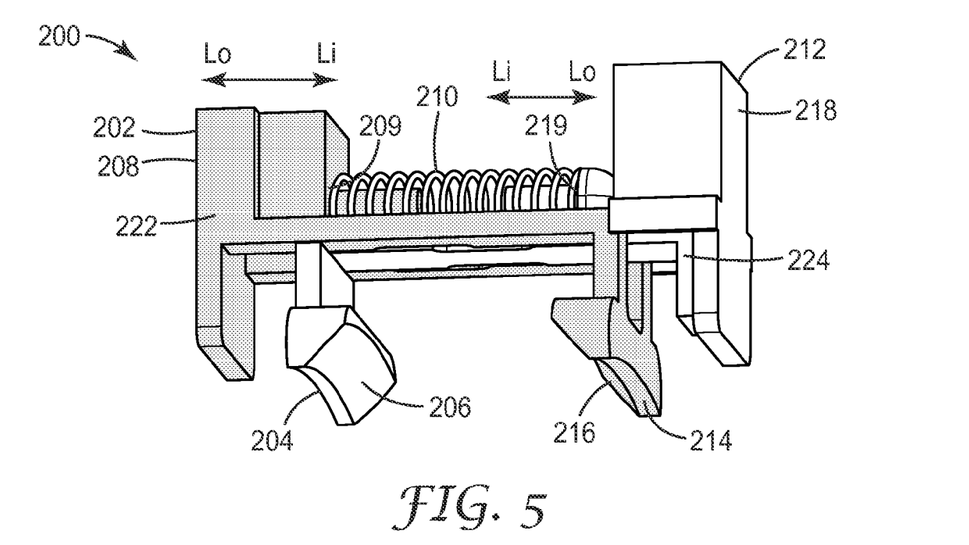
FIG. 5 is a rear perspective view of a portion of an exemplary carriage.

Fins 204 and 214 may be movable toward each other and away from each other. One such manner in which this may be achieved is shown in FIG. 5 (in which some components of the carriage that are visible in FIG. 3, such as a bracket, bolt and adjustment knob discussed later herein, are omitted for ease of presentation). Fins 204 and 214 of the general type shown in FIG. 5 may be movable laterally inwards toward each other into the first, engaged position, and movable laterally away from each other into a second, disengaged position in which they are sufficiently far apart from each other to allow carriage 200 to be engaged onto, or disengaged from, elongated guide 100. That is, when the fins are in the second, disengaged position, they are further apart from each other than the distance between the laterally outermost edges 118a and 118b of radially outward, laterally-flared flange 114, as least at some point along the elongate length of the guide. Fins 204 and 214 may be biased toward each other, so that in the absence of any force exerted by the user, the fins will be urged into the first, engaged position. This may be achieved e.g. by the use of a biasing member (e.g., spring) 210 as shown in FIG. 4, which biasing member is seated onto first and second seats 209 and 219 (with bosses provided thereon to retain the biasing member in place). It will be apparent that the design of the exemplary carriage of FIG. 3 provides that the laterally outward force exerted on seats 209 and 219 by biasing member 210 causes fins 204 and 214 to be urged laterally inward, towards each other.

In some embodiments, carriage 200 may be configured so that a user can manually actuate (manipulate) the carriage so as to overcome the biasing force and motivate the fins to the second, disengaged position. This can be done e.g. in order to disengage the carriage (and visor connected thereto) from the elongated guide. This may be performed, for example, by providing tabs 208 and 218 that are respectively connected to fins 214 and 204, so that applying a laterally inward force to a tab causes the fin connected thereto to move laterally outward. In the exemplary embodiment of FIG. 5, this is achieved by providing fin 214 and tab 208 as parts of the same contiguous carriage piece 222 (shown grey-shaded in FIG. 5), and providing fin 204 and tab 218 as parts of the same contiguous carriage piece 224 (shown unshaded in FIG. 5).) Thus, a user may use his or her fingers to squeeze carriage tabs 208 and 218 inward toward each other to motivate fins 214 and 204 to the second, disengaged position. In some embodiments, such a procedure may also be used in order to engage the carriage with the elongated guide. That is, a user may squeeze tabs 208 and 218 toward each other so as to move fins 214 and 204 laterally outwards from each other, and may then move carriage 200 (from a position radially outward of elongated guide 100) generally radially inward toward the guide until fins 204 and 214 are in a position to respectively enter channels 116a and 116b, at which time the user may release the squeezing pressure on the carriage. It will be appreciated, of course, that other arrangements can be used. For example, a carriage might be configured in which squeezing a tab on one lateral side of the carriage causes a fin on that same lateral side of the carriage to be moved laterally outward (rather than causing a fin on the laterally opposite side of the carriage to be moved laterally outward, as in the design of FIG. 5). Furthermore, any suitable actuatable member(s) (e.g., tab, surface, knob, etc.), and actuating motion thereof (e.g., outward-separating, rotating, lifting, etc.), can be used in place of inwardly-squeezable tabs 208 and 218.

In some embodiments, carriage 200 may be configured so that moving the carriage from a position radially outward of elongated guide 100, generally radially inward toward the guide, automatically overcomes the biasing force and urges the fins laterally away from each other so that the carriage can be engaged with the elongated guide. By automatically is meant that the action of moving the carriage radially inward causes the desired engaging, without the user having to perform any manipulation such as squeezing tabs of carriage 200, turning a knob, manipulating a handle, etc. This may be achieved e.g. by providing fins 204 and 214 respectively with laterally-inward-facing surfaces 206 and 216 that are beveled (that is, are angled so as to be further apart toward the terminal tips of the fins). This can have the result that when carriage 200 is brought into contact with elongated guide 100, the laterally-outwardmost edges 118*a* and 118*b* press against beveled surfaces 206 and 216 to overcome the biasing force and cause fins 204 and 214 to move laterally outwardly from each other to a sufficient distance to allow the carriage to be engaged with the elongated guide. Once the radially-outwardmost portions of the fins move radially-inwardly past flange 114 of the elongated guide, the laterally-outward force is removed and the biasing force causes the fins to return to the first, engaged position. It will be evident that such arrangements advantageously allow a carriage (and a visor attached thereto) to be quickly and easily engaged with, and mounted onto, an elongated guide, merely by the act of moving the carriage generally radially inward into contact with the elongated guide.

The above-discussed arrangements allow a visor to be moved forward and rearward generally along a long axis of an elongated guide, e.g. by way of a carriage that slidably moves along the guide and to which the visor is connected. In some embodiments, it may be useful to also provide that the angle of the visor with respect to the carriage may be adjustable. Thus, in such embodiments the visor may be rotatably connected to the carriage, e.g. around an axis that is perpendicular to the sagittal plane of the hardhat (when the elongated guide is attached to the hardhat). One such way of providing such a function is illustrated in FIGS. 1 and 3. In this exemplary arrangement, bracket 236 (which serves to hold and secure visor 300) of carriage 200 is rotatably connected to the remaining portion of carriage 200. In the illustrated arrangement, this is provided in a manner in which the ease of rotating visor 300 relative to carriage 200 can be manually adjusted by the user as desired. To achieve this, either or both of members 238 and 239 of bracket 236 may comprise teeth 237 that intermesh with teeth 232 of carriage 200. Teeth 237 and 232 comprise through-holes that are aligned so as to allow bolt 233 to pass therethrough, which bolt comprises adjustment knob 243 that can be tightened or loosened to increase or decrease the force with which the intermeshed teeth 232 and 237 are held against each other. In this manner, the force required to rotate bracket 236 (and thus visor 300) relative to carriage 200 may be set as desired. It will be appreciated, of course, that this is merely one convenient way of achieving such a rotatable connection and that any rotatable connection may be used, which may be made adjustable in any suitable way. For example, such a rotatable connection may comprise a ratcheted connection or the like. Any such rotatable connection can allow the angle of the visor relative to the carriage to extend over any desired range. In various embodiments, the angle over which such rotation of the visor relative to the carriage may extend, can range from e.g. at least 10, 20, or 30 degrees, to at most 190, 90, 60, or 40 degrees. It will be appreciated that the presence of a rotatable connection between a visor and a carriage can provide that an elongated guide can slidably support a visor so that the visor can be moved in a first, generally arcuate translational motion (i.e., can be slidably moved along the (arcuate) long axis of the visor), and so that the visor can also be moved in a second, purely rotational motion (i.e., can be rotated about a rotatable connection between the visor and a carriage to which the visor is attached and that is slidably supported by the elongated guide).

Figure 10:
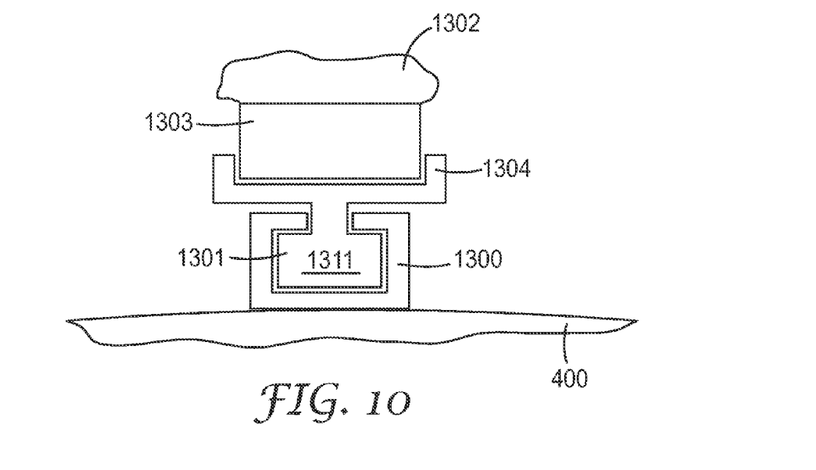
FIG. 10 is a representation in generic cross-sectional view, of another exemplary elongated guide and another exemplary carriage slidably supported thereby.

In some embodiments, the location of the first, shielding position of the visor may be adjustable along at least a portion of the long axis of the elongated guide. One such way of achieving this is shown in exemplary manner in FIG. 6. In the depicted design, a forward section 102 of the elongated guide 100 comprises an elongated slot 172 that is generally aligned with the long axis of guide 100 and into which may be mated positionable insert 174 (which is shown exploded away from guide 100, in FIG. 10). Slot 172 and insert 174 comprise a complementary arrangement of teeth 173 and 175 that allow insert 174 to be mated to the elongated guide at any suitable position along the long axis of slot 172. Insert 174 is also arranged so that it can be secured in place to elongated guide 100 by way of laterally outward flanged edges that are configured so as to be snap-fittable to the laterally outward edges of guide 100. When insert 174 is in place on forward section 102 of elongated guide 100, the inset provides a physical barrier that interferes with any further forward movement of carriage 200 along elongated guide 100 and that thus provides a forward end-stop. Insert 174 can be placed at any position along the length of elongated slot 172, in order to set the position of the forward end-stop. It will be appreciated, of course, that these are merely exemplary designs and that any suitable design that allows an adjustable forward end-stop to be provided, may be used with the methods disclosed herein. Although not shown herein, an adjustable rear end-stop may also be used if desired.

Further aspects of the use of an elongated guide will now be discussed with respect to FIGS. 7 and 8. As previously mentioned, FIG. 7 depicts a generic representation (in cross-section) of an elongated guide 100, and a carriage 200, of the general type shown in FIGS. 1-3 (for ease of presentation, parts of the carriage that are movable relative to each other are not individually distinguished). In designs of this type, the elongated guide is seen to take the form of an elongated rail with a radially-outward, laterally-flared flange 114. Flange 114 (specifically, radially-inward facing surfaces 115*a* and 115*b* thereof) serves to keep carriage 200 in its engaged configuration even as carriage 200 is slidably moved along the elongate length of the guide. It will be appreciated that such designs fall in a general category in which a carriage comprises two laterally-opposing portions (e.g., fins) that can be snap-fitted (by the application of sufficient force) onto a flanged rail (e.g., a rib with an enlarged head). It will be appreciated that many variations of such designs are possible and are encompassed by the general disclosures presented herein (for example, a biasing force can be built into carriage and fins thereof, as made, rather than using e.g. a separately provided biasing spring).

However, the above-described general types of guide and carriage are not the only type that may be used. Thus, in FIG. 8 is shown another design (again, in generic representation in cross-section), in which an elongated guide 1100 comprises first and second elongated rails 1101 and 1102, each with a long axis that is generally aligned with the long axis of elongated guide 1100. (Rails 1101 and 1102 do not necessarily have to be connected to each other by a base portion in the manner shown in FIG. 8; rather, they could each be separately attached to a hardhat.) The two elongated rails are laterally separated from each other along at least a majority of the length of the elongated guide, with each rail comprising a radially-outwardly-extending rib (1103 and 1104, respectively) comprising a radially-outward flange (1105 and 1106, respectively) that is laterally-inwardly flared as shown in FIG. 8. In such an arrangement, the two elongated rails 1101 and 1102 collectively define an elongated interior channel 1111, noting that interior channel 1111 comprises a radially-outward-facing, elongated opening 1112 defined by the laterally inward edges of flanges 1105 and 1106. With this elongated guide may be used carriage 1200, which comprises an engaging member 1201 that is insertable into interior channel 1111 of elongated guide 1100 and that is slidably movable through interior channel 1111, along the long axis of the elongated guide. Such a carriage and elongated guide may allow a visor that is connected (e.g., rotatably connected) to the carriage, to be slidably moved along the long axis of the guide. (If desired, radially-inward and/or radially-outward surfaces of engaging member 1201 may be curved so as to at least approximately match the curvature of the elongated guide, to enhance the ease of slidably moving member 1201 thorough interior channel 1111 of the guide.)

Figure 8:
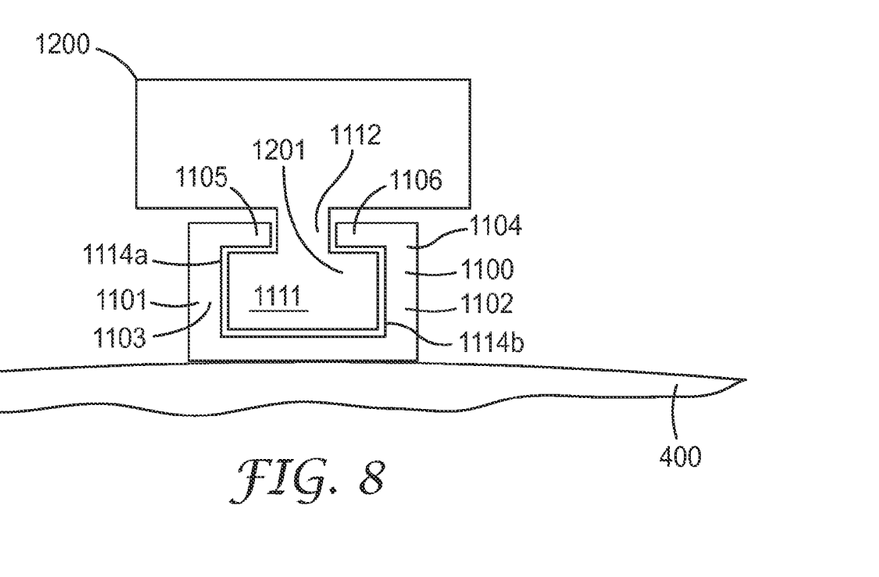
FIG. 8 is a representation in generic cross-sectional view, of another exemplary elongated guide and another exemplary carriage slidably supported thereby.
Figure 9:
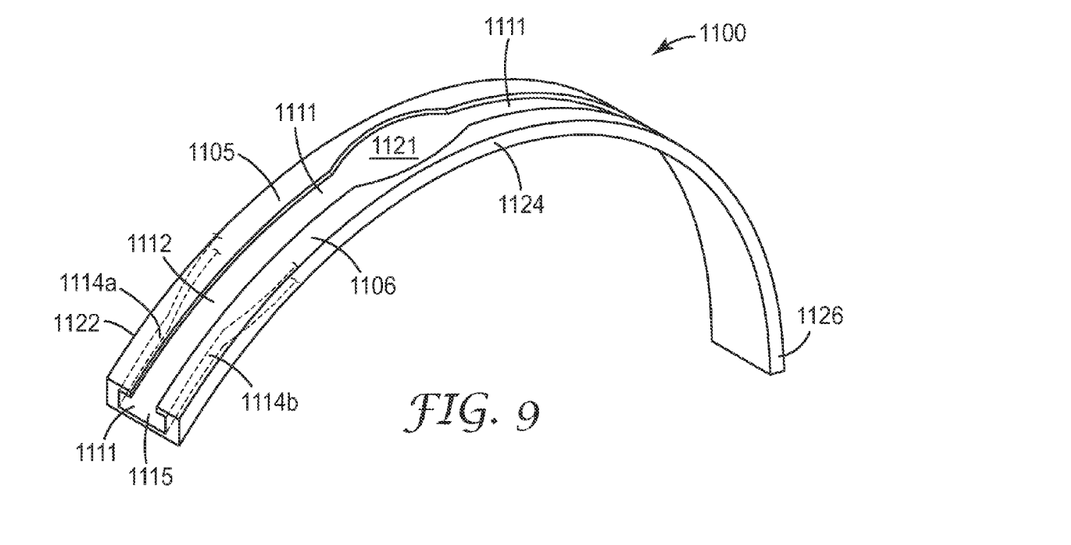
FIG. 9 is a front-side perspective view of another exemplary elongated guide.

A particular elongated guide of the general type shown in FIG. 8, is shown in perspective view in FIG. 9. In this view, radially-outward, elongate opening 1112 of channel 1111 comprises, along the majority of the length of the elongated guide, a lateral width that is too small to allow engaging member 1201 of carriage 1200 to pass radially outwardly therethrough. However, in a selected portion of the elongated length of the guide, the laterally inward edges of flanges 1105 and 1106 veer generally laterally outward to form flared, radially-outward-facing opening 1121, the lateral width of which opening is sufficient to allow engaging member 1201 to pass therethrough.

Such an arrangement provides another way in which a carriage may be engageable with an elongated guide (into a configuration in which the carriage is slidably supported by the elongated guide) by way of moving the carriage generally radially inward toward the elongated guide from a position radially outward of the elongated guide. That is, carriage 1200 may be positioned so that engaging member 1201 is radially outward of flared opening 1121 of elongated guide 1100, and then carriage 1200 may be moved generally radially inward toward guide 1100 so that engaging member 1201 passes through flared opening 1121 and into interior channel 1111 of guide 1100. Carriage 1200 (e.g., with a visor connected thereto) can then be slidably moved forward and rearward along elongated guide 1100. It will be appreciated that the concept of moving a carriage generally radially inward is not limited to moving the carriage in a direction that is purely normal to the long axis of the elongated guide (at that point along the elongated length of the guide). That is, this concept includes cases in which the direction of motion is at a non-normal angle to the long axis as long as it is at least generally toward the concave side of the elongated guide.

Generally as illustrated in FIG. 9, in some embodiments flared opening 1121 may be positioned between a first, forward position of carriage 1200 (which would correspond to a shielding position of a visor that is connected to the carriage), and a second, rearward position of carriage 1200 (which would correspond to a retracted position of a visor that is connected to the carriage). In such embodiments, the carriage may be slidably moved back and forth past flared opening 1121, with the force of gravity on the carriage and visor serving to hold the carriage down so that engaging member 1201 of the carriage remains within channel 1111 as the carriage moves past opening 1121 (so that the carriage remains engaged with the guide). When a user desires to disengage the carriage (e.g., in order to remove the visor from the elongated guide), the user may stop the carriage with engaging member 1201 aligned with flared opening 1121 and then lift the carriage radially outward. One or more features (e.g., detents, bumps, or the like) may be provided in the guide to assist the user in determining when the engaging member of the carriage is aligned with the flared opening. In other embodiments, flared opening 1121 may be located rearward of the second position of the carriage (that corresponds to a retracted position of the visor connected thereto). In such case, the user may slide the carriage rearward to the second position in order to retract the visor. The guide (and/or carriage) may comprise features (e.g., detents, bumps of the like) so that the carriage may be seated in this second position and may require an extra rearward-directed force to motivate the carriage rearward beyond the second position in order to reach the flared opening in order to disengage the carriage.

FIG. 9 also depicts another general feature that may be useful. In addition to, or in place of, the above-mentioned arrangements in which a carriage may be held in the first, forward position solely by the force of gravity acting on the carriage and visor, and/or in which a latch is used to hold the carriage in the first position, an elongated guide may be designed so that interior channel 1111 becomes narrower in a forward section 1122 of the elongated guide. That is, in this forward section, channel 1111 may be narrower than it is e.g. in a crown (middle) section 1124 of the guide, so that in this forward section 1122 the channel comprises a "neck" 1115 that enhances, e.g. by friction against engaging member 1201, the holding of the carriage in the first position. This is achieved in the exemplary embodiment of FIG. 9 by locating lateral walls 1114a and 1114b of the guide laterally closer to each other in forward section 1122 of the guide, than they are e.g. in crown section 1126 of the guide. If desired, the shape of engaging member 1201 may be selected to enhance such an effect. For example, an engaging member might be generally wedge or V-shaped with a narrow front end, which shape may generally match the shape of neck 1115.

Such arrangements may similarly be used in the rear section 1126 of the elongated guide, e.g. to enhance the holding of the carriage/visor in the second, refracted position. It will also be recognized that such geometric and/or frictional enhancement of the holding of a carriage in a desired location can be achieved in other ways than by controlling the lateral width of an interior channel. For example, the (radially inward-outward) height of such a channel might be controlled to similar effect. Beyond this, it will be appreciated that such methods can also be used with the earlier-described elongated guides (e.g., that correspond in general to an I-beam design). For example, the clearance between upper and lower flanges of such a guide, the width of the rib of such a guide, etc., could be controlled in similar manner to enhance, e.g. frictionally enhance, the holding of a carriage at a desired position.

Still other configurations are encompassed within the designs disclosed herein. For example, the exemplary design shown in representative cross-sectional format in FIG. 10 generically depicts an elongated guide 1300 that defines an elongated channel 1311 (which may be generally similar to the above-described channel 1111). Guide 1300 further comprises carriage 1304, that is slidably supported by guide 1300 but that, because it comprises member 1301 that is non-removably inserted into channel 1311 (e.g. in the manufacture of guide 1300) is not disengagable from guide 1300. Carriage 1304 further comprises connection 1303 to visor 1302 (all of which are shown in generic representation in FIG. 10).

Thus, in embodiments of this general type a carriage is provided that is slidably movable along a guide but is not disengagable therefrom. So, in order to provide that a visor is removably mountable to such a guide, connection 1303 may advantageously be a removable (i.e., disconnectable) connection. Such an arrangement may be achieved by any suitable design. For example, visor 1302 might comprise a connection plate that can be coupled into a receiving slot of carriage 1304, and that may be decoupled therefrom when desired by the user. Of course, a removable connection between such a visor and carriage may also be a rotatable connection, if desired. It will thus be appreciated that, in various embodiments, a carriage may be removably engaged with an elongated guide and non-removably connected to a visor; or, it may be non-removably engaged with an elongated guide and removably connected to the visor. Either circumstance can provide the desired removable mounting of a visor to an elongated guide. Of course, a carriage may be both removably engaged with an elongated guide, and removably connected to a visor, if desired.

It will be appreciated that (irrespective of which of the above-disclosed exemplary designs might be used), in at least some embodiments no part of the elongated guide is integral with the hardhat (with "integral" meaning comprised of the same material as the hardhat shell and made in the same forming (e.g., molding) operation). In further embodiments, no part of the elongated guide is non-removably attached to the hardhat. However, such conditions do not preclude the presence of complementary or cooperating features on the hardhat that facilitate or enhance the attaching of the elongated guide to the hardhat, or that serve to enhance the ability of the elongated guide to remain in place on the hardhat. For example, a hardhat might be provided with a sagittal groove or channel, or one or more recesses located generally along or near the sagittal plane, into which one or more radially-inward portions of the elongated guide may be seated.

In at least some embodiments the visor is not rotatably or slidably supported by any item other than the elongated guide and is not rotatably or slidably connected to the hardhat by way of any component other than the elongated guide (and a carriage functioning therewith). Thus, in such embodiments a hinged connection of the visor to the hardhat, e.g. in the temple/ear area of the hardhat, is not needed. It will be recognized that the absence of any hinged connection between the visor and the hardhat in the temple/ear area of the visor may provide that the motion of (any arbitrarily-picked location on) the visor may not be limited to a purely circular arc (around an axis of rotation provided by such a hinged connection), as it would be if the visor comprised such a hinged connection. The absence of any need to support a temple/ear area of a visor (e.g., area 308 of visor 300 of FIG. 1), means that such an area can be minimized (or even essentially omitted). This may provide that at least an ear area of a hardhat (e.g., area 408 of hardhat 400 of FIG. 1) may be unobstructed by the visor, so that other components (e.g., hearing protection muffs, headphones, etc.) may be fitted to the ear area of the hardhat as desired.

An elongated guide as disclosed herein may be provided already attached to a hardhat, or may be provided separately from a hardhat. Similarly, an elongated guide may be provided with a visor already mounted to the guide. Or, an elongated guide may be provided separately from a visor. In some embodiments, a kit may be provided that comprises at least one elongated guide as disclosed herein, and at least one visor. In further embodiments, such a kit may include multiple, non-identical visors (e.g., visors with different shade numbers, one or more visors for welding protection and one or more grinding visors, and so on). In some embodiments, such a kit may comprise at least one hardhat.

Also disclosed herein is a method of adapting a hardhat for eye-protected operation, the method comprising removably attaching an elongated guide to the hardhat so that a long axis of the elongated guide is at least generally coincident with a sagittal plane of the hardhat; and, removably mounting a visor on the elongated guide so that the visor is slidably supported by the elongated guide so as to be slidably movable generally along the long axis of elongated guide between at least a first, shielding position and a second, retracted position. It will be appreciated that such methods may be used to retrofit (e.g., in the field) an elongated guide and visor to an existing hardhat. Or, such methods may be used to fit an elongated guide and visor to a hardhat that is supplied (e.g., in a kit) with the guide and visor. Or, a hardhat, elongated guide and visor can be supplied to a user as a preassembled assembly.

LIST OF EXEMPLARY EMBODIMENTS

Embodiment 1. An elongated guide that is removably attachable to a hardhat so that a long axis of the elongated guide is at least generally coincident with a sagittal plane of the hardhat, wherein the elongated guide is configured to slidably support a visor that is removably mountable to the elongated guide so that the visor is slidably movable along the long axis of the elongated guide between at least a first, shielding position and a second, retracted position.

Embodiment 2. The elongated guide of embodiment 1 further comprising a visor that is removably mounted to, and slidably supported by, the elongated guide.

Embodiment 3. The elongated guide of embodiment 2 wherein the visor is removably mounted to, and slidably supported by, the elongated guide, by way of at least one carriage that is connected to the visor and that is engaged with, and slidably supported by, the elongated guide.

Embodiment 4. The elongated guide of embodiment 3 wherein the carriage is removably engaged with the elongated guide and is non-removably connected to the visor.

Embodiment 5. The elongated guide of embodiment 3 wherein the carriage is non-removably engaged with the elongated guide and is removably connected to the visor.

Embodiment 6. The elongated guide of any of embodiments 3-4 wherein the elongated guide and the carriage are configured so that the carriage is engageable with the elongated guide into a configuration in which the carriage is slidably supported by the elongated guide, by moving the carriage generally radially inward toward the elongated guide from a position radially outward of the elongated guide.

Embodiment 7. The elongated guide of any of embodiments 3-6 wherein the elongated guide comprises an elongated rail with an elongated rib with long axis that defines the long axis of the elongated guide and wherein the elongated rib comprises a radially-outward, laterally-flared flange.

Embodiment 8. The elongated guide of embodiment 7 wherein the radially-outward, laterally-flared flange of the elongated rail at least partially defines first and second elongated channels that respectively laterally outwardly flank first and second sides of the elongated rib, and wherein the carriage comprises first and second laterally-inwardly-facing, oppositely-facing fins, that are configured so that when the fins are in a first, engaged position at least portions of the fins extend sufficiently laterally inwards into the first and second elongated channels to maintain the carriage in an engaged condition with the elongated rail.

Embodiment 9. The elongated guide of any of embodiments 7-8 wherein the first and second laterally-inwardlyfacing, oppositely-facing fins of the carriage are movable with respect to each other between a second, disengaged position in which the fins are laterally separated by a distance sufficient to allow the carriage to be radially-outwardly disengaged from the elongated guide, and the first, engaged position.

Embodiment 10. The elongated guide of embodiment 9 wherein the fins are biased with a biasing force toward the first, engaged position, and wherein a laterally-inward-facing surface of the first fin, and a laterally-inward-facing surface of the second fin, are each beveled so that moving the carriage radially downward toward the elongated guide from a position radially above the elongated guide causes laterally-outwardmost edges of the radially-outward, laterally-flared flange of the elongated rail to press laterally outwardly against the laterally-inward-facing surfaces of the fins so as to automatically overcome the biasing force and to motivate the fins to move laterally outwardly away from each other to a sufficient distance to allow the carriage to be engaged with the elongated rail.

Embodiment 11. The elongated guide of embodiment 10 wherein the carriage is configured so that a user can manually manipulate the carriage so as to apply a predetermined force sufficient to overcome the biasing force so as to motivate the fins from the first, engaged position into the second, disengaged position.

Embodiment 12. The elongated guide of embodiment 6 wherein the elongated guide comprises two elongated rails each with a long axis that is generally aligned with the long axis of the elongated guide, the two elongated rails being laterally separated from each other along at least a majority of the length of the elongated guide, and wherein each rail comprises a radially-outwardly-extending rib comprising a radially-outward flange that is laterally-inwardly flared, so that the two elongated rails collectively define an interior channel into which an engaging member of the carriage is insertable and within which the engaging member is slidably movable along the long axis of the elongated guide.

Embodiment 13. The elongated guide of any of embodiments 2-12 wherein the carriage is rotatably connected to the visor around an axis that is perpendicular to the sagittal plane of the hardhat when the elongated guide is attached to the hardhat.

Embodiment 14. The elongated guide of any of embodiments 3-13 wherein the elongated guide comprises a first, forward end-stop that prevents forward movement of the carriage along the long axis of the elongated guide past a first predetermined location proximate to a first, forward end of the elongated guide and thus establishes the first, shielding position of the visor, and wherein the first, forward end-stop is an adjustable end-stop whose position can be adjusted forward and rearward along a portion of the long axis of the elongated guide.

Embodiment 15. The elongated guide of any of embodiments 3-14 wherein the elongated guide comprises a second, rearward end-stop that prevents rearward movement of the carriage along the long axis of the guide past a second predetermined location distal to the first, forward end of the elongated guide and thus establishes the second, refracted position of the visor, and wherein the second, rearward end-stop comprises a latch configured so that positioning the carriage at the second predetermined location automatically activates the latch to secure the carriage at the second predetermined location until the latch is manually released by a user.

Embodiment 16. The elongated guide of any of embodiments 1-15 further comprising a hardhat to which the elongated guide is removably attached.

Embodiment 17. The elongated guide of embodiment 16 wherein a forward section of the elongated guide is removably attached to a front brim of the hardhat by way of a forward attachment mechanism of the elongated guide, and wherein a rearward section of the elongated guide is removably attached to a rear rim of the hardhat by way of a rearward attachment mechanism of the elongated guide.

Embodiment 18. The elongated guide of embodiment 17 wherein the rearward attachment mechanism of the elongated guide is an adjustable attachment mechanism that adjustably attaches the rearward section of the elongated guide to the rear rim of the hardhat.

Embodiment 19. The elongated guide of any of embodiments 16-18 wherein no part of the elongated guide is integral with the hardhat or is permanently attached thereto.

Embodiment 20. The elongated guide of any of embodiments 16-19 further comprising a visor that is removably mounted to the elongated guide and is slidably supported thereby, by way of at least one carriage that is connected to the visor.

Embodiment 21. The elongated guide of embodiment 20 wherein the visor is not rotatably or slidably supported by any component other than the elongated guide and is not rotatably or slidably connected to the hardhat by way of any component other than the guide.

Embodiment 22. A kit comprising at least one elongated guide of any of embodiments 1-21 and at least one visor that is removably mountable to the elongated guide and is slidably supportable thereby, so that when removably mounted to the elongated guide the visor is slidably movable along the elongated guide between at least a first, shielding position and a second, retracted position.

Embodiment 23. The kit of embodiment 22 further comprising at least one hardhat to which the elongated guide is detachably attachable.

Embodiment 24. The kit of any of embodiments 22-23 wherein the kit includes multiple non-identical visors.

Embodiment 25. A method of adapting a hardhat for eye-protected operation, the method comprising: removably attaching the elongated guide of any of embodiments 1-21 to the hardhat so that a long axis of the elongated guide is at least generally coincident with a sagittal plane of the hardhat; and, removably mounting a visor on the elongated guide so that the visor is slidably supported by the elongated guide so as to be slidably movable generally along the long axis of elongated guide between at least a first, shielding position and a second, retracted position.

EXAMPLES

Prototypes of elongated guides and of carriages, of the types illustrated in FIGS. 1-3, were produced and were attached to commercially available hardhats. Commercially available welding visors (e.g., those available from 3M Company, St. Paul Minn. under the trade designation SPEEDGLAS) were modified as needed so that they could be attached to a carriage bracket of the type shown in FIGS. 1-3. Other working prototypes were also produced of the general type illustrated in FIGS. 8-10. Working prototypes were thus produced of various designs, in which elongated guides could be removably attached to hardhats, and in which visors could be removably mounted to the elongated guides and could be slidably moved back and forth along the guides.

The tests and test results described above are intended solely to be illustrative, rather than predictive, and variations in the testing procedure can be expected to yield different results. The foregoing detailed description and examples have been given for clarity of understanding only. No unnecessary limitations are to be understood therefrom. It will be apparent to those skilled in the art that the specific exemplary structures, features, details, configurations, etc., that are disclosed herein can be modified and/or combined in numerous embodiments. All such variations and combinations are contemplated by the inventor as being within the bounds of the conceived invention not merely those representative designs that were chosen to serve as exemplary illustrations. Thus, the scope of the present invention should not be limited to the specific illustrative structures described herein, but rather extends at least to the structures described by the language of the claims, and the equivalents of those structures.

What is claimed is:

1. An elongated guide that is removably attachable to a hardhat so that a long axis of the elongated guide is at least generally coincident with a sagittal plane of the hardhat, wherein the elongated guide is configured to slidably support a visor that is removably mountable to the elongated guide so that the visor is slidably movable along the long axis of the elongated guide between at least a first, shielding position and a second, retracted position;
and wherein the elongated guide further comprises a visor that is removably mounted to, and slidably supported by, the elongated guide, by way of at least one carriage that is rotatably connected to the visor around an axis that is perpendicular to the sagittal plane of the hardhat when the elongated guide is attached to the hardhat and that is engaged with, and slidably supported by, the elongated guide.

2. The elongated guide of claim 1 wherein the carriage is removably engaged with the elongated guide and is non-removably connected to the visor.

3. The elongated guide of claim 1 wherein the carriage is non-removably engaged with the elongated guide and is removably connected to the visor.

4. The elongated guide of claim 1 wherein the elongated guide and the carriage are configured so that the carriage is engageable with the elongated guide into a configuration in which the carriage is slidably supported by the elongated guide, by moving the carriage generally radially inward toward the elongated guide from a position radially outward of the elongated guide.

5. The elongated guide of claim 1 wherein the elongated guide comprises an elongated rail with an elongated rib with long axis that defines the long axis of the elongated guide and wherein the elongated rib comprises a radially-outward, laterally-flared flange.

6. The elongated guide of claim 1 wherein the elongated guide comprises two elongated rails each with a long axis that is generally aligned with the long axis of the elongated guide, the two elongated rails being laterally separated from each other along at least a majority of the length of the elongated guide, and wherein each rail comprises a radially-outwardly-extending rib comprising a radially-outward flange that is laterally-inwardly flared, so that the two elongated rails collectively define an interior channel into which an engaging member of the carriage is insertable and within which the engaging member is slidably movable along the long axis of the elongated guide.

7. The elongated guide of claim 1 wherein the elongated guide comprises a first, forward end-stop that prevents forward movement of the carriage along the long axis of the elongated guide past a first predetermined location proximate to a first, forward end of the elongated guide and thus establishes the first, shielding position of the visor, and wherein the first, forward end-stop is an adjustable end-stop whose position can be adjusted forward and rearward along a portion of the long axis of the elongated guide.

8. The elongated guide of claim 1 wherein the elongated guide comprises a second, rearward end-stop that prevents rearward movement of the carriage along the long axis of the guide past a second predetermined location distal to the first, forward end of the elongated guide and thus establishes the second, retracted position of the visor, and wherein the second, rearward end-stop comprises a latch configured so that positioning the carriage at the second predetermined location automatically activates the latch to secure the carriage at the second predetermined location until the latch is manually released by a user.

9. The elongated guide of claim 1 further comprising a hardhat to which the elongated guide is removably attached.

10. The elongated guide of claim 9 wherein a forward section of the elongated guide is removably attached to a front brim of the hardhat by way of a forward attachment mechanism of the elongated guide, and wherein a rearward section of the elongated guide is removably attached to a rear rim of the hardhat by way of a rearward attachment mechanism of the elongated guide.

11. The elongated guide of claim 1 wherein the visor is not rotatably or slidably supported by any component other than the elongated guide and is not rotatably or slidably connected to the hardhat by way of any component other than the elongated guide.

12. An elongated guide that is removably attachable to a hardhat so that a long axis of the elongated guide is at least generally coincident with a sagittal plane of the hardhat,
wherein the elongated guide comprises an elongated rail with an elongated rib with long axis that defines the long axis of the elongated guide and wherein the elongated rib comprises a radially-outward, laterally-flared flange and wherein the elongated guide is configured to slidably support a visor that is removably mountable to the elongated guide so that the visor is slidably movable along the long axis of the elongated guide between at least a first, shielding position and a second, retracted position;
and wherein the elongated guide further comprises a visor that is removably mounted to, and slidably supported by, the elongated guide, by way of at least one carriage that is engaged with, and slidably supported by, the elongated guide.

13. The elongated guide of claim 12 wherein the radially-outward, laterally-flared flange of the elongated rail at least partially defines first and second elongated channels that respectively laterally outwardly flank first and second sides of the elongated rib, and wherein the carriage comprises first and second laterally-inwardly-facing, oppositely-facing fins, that are configured so that when the fins are in a first, engaged position at least portions of the fins extend sufficiently laterally inwards into the first and second elongated channels to maintain the carriage in an engaged condition with the elongated rail.

14. The elongated guide of claim 13 wherein the first and second laterally-inwardly-facing, oppositely-facing fins of the carriage are movable with respect to each other between a second, disengaged position in which the fins are laterally separated by a distance sufficient to allow the carriage to be radially-outwardly disengaged from the elongated guide, and the first, engaged position.

15. The elongated guide of claim 14 wherein the fins are biased with a biasing force toward the first, engaged position, and wherein a laterally-inward-facing surface of the first fin, and a laterally-inward-facing surface of the second fin, are each beveled so that moving the carriage radially downward toward the elongated guide from a position radially above the elongated guide causes laterally-outwardmost edges of the radially-outward, laterally-flared flange of the elongated rail to press laterally outwardly against the laterally-inward-facing surfaces of the fins so as to automatically overcome the biasing force and to motivate the fins to move laterally outwardly away from each other to a sufficient distance to allow the carriage to be engaged with the elongated rail.

16. The elongated guide of claim 15 wherein the carriage is configured so that a user can manually manipulate the carriage so as to apply a predetermined force sufficient to overcome the biasing force so as to motivate the fins from the first, engaged position into the second, disengaged position.

17. The elongated guide of claim 12 wherein the carriage is rotatably connected to the visor around an axis that is perpendicular to the sagittal plane of the hardhat when the elongated guide is attached to the hardhat.

18. The elongated guide of claim 12 further comprising a hardhat to which the elongated guide is removably attached.

19. An elongated guide that is removably attachable to a hardhat so that a long axis of the elongated guide is at least generally coincident with a sagittal plane of the hardhat, wherein the elongated guide is configured to slidably support a visor that is removably mountable to the elongated guide so that the visor is slidably movable along the long axis of the elongated guide between at least a first, shielding position and a second, retracted position;
the elongated guide comprising a hardhat to which the elongated guide is removably attached, wherein a forward section of the elongated guide is removably attached to a front brim of the hardhat by way of a forward attachment mechanism of the elongated guide, and wherein a rearward section of the elongated guide is removably attached to a rear rim of the hardhat by way of a rearward attachment mechanism of the elongated guide.

20. The elongated guide of claim 19 wherein the rearward attachment mechanism of the elongated guide is an adjustable attachment mechanism that adjustably attaches the rearward section of the elongated guide to the rear rim of the hardhat.

21. The elongated guide of claim 19 wherein no part of the elongated guide is integral with the hardhat or is permanently attached thereto.

22. The elongated guide of claim 19 further comprising a visor that is removably mounted to the elongated guide and is slidably supported thereby, by way of at least one carriage that is connected to the visor.

23. The elongated guide of claim 19 wherein the visor is not rotatably or slidably supported by any component other than the elongated guide and is not rotatably or slidably connected to the hardhat by way of any component other than the elongated guide.

24. The elongated guide of claim 19 wherein the elongated guide comprises an elongated rail with an elongated rib with long axis that defines the long axis of the elongated guide and wherein the elongated rib comprises a radially-outward, laterally-flared flange.

25. The elongated guide of claim 19 wherein the elongated guide comprises two elongated rails each with a long axis that is generally aligned with the long axis of the elongated guide, the two elongated rails being laterally separated from each other along at least a majority of the length of the elongated guide, and wherein each rail comprises a radially-outwardly-extending rib comprising a radially-outward flange that is laterally-inwardly flared, so that the two elongated rails collectively define an interior channel into which an engaging member of the carriage is insertable and within which the engaging member is slidably movable along the long axis of the elongated guide.

* * * * *

UNITED STATES PATENT AND TRADEMARK OFFICE
CERTIFICATE OF CORRECTION

| | |
|---|---|
| PATENT NO. | : 8,701,212 B2 |
| APPLICATION NO. | : 13/627571 |
| DATED | : April 22, 2014 |
| INVENTOR(S) | : Björn Daniels |

Page 1 of 1

It is certified that error appears in the above-identified patent and that said Letters Patent is hereby corrected as shown below:

In the Specification

Column 2
Line 32, Delete "refracted" and insert -- retracted --, therefor.

Column 6
Line 25, Delete "refracted" and insert -- retracted --, therefor.

Column 15
Line 61, Delete "refracted" and insert -- retracted --, therefor.

Signed and Sealed this
Sixth Day of January, 2015

Michelle K. Lee
*Deputy Director of the United States Patent and Trademark Office*